US009283337B2

(12) United States Patent
Lastow et al.

(10) Patent No.: US 9,283,337 B2
(45) Date of Patent: Mar. 15, 2016

(54) DISPENSER AND METHOD FOR ENTRAINING POWDER IN AN AIRFLOW

(75) Inventors: Orest Lastow, Lund (SE); Johan Remmelgas, Mölndal (SE); John Briant, Baldock (GB)

(73) Assignee: Astrazeneca AB, Sodertalje (SE)

( * ) Notice: Subject to any disclaimer, the term of this patent is extended or adjusted under 35 U.S.C. 154(b) by 933 days.

(21) Appl. No.: 12/809,155

(22) PCT Filed: Dec. 18, 2008

(86) PCT No.: PCT/SE2008/051490
§ 371 (c)(1),
(2), (4) Date: Dec. 7, 2010

(87) PCT Pub. No.: WO2009/082343
PCT Pub. Date: Jul. 2, 2009

(65) Prior Publication Data
US 2011/0083667 A1 Apr. 14, 2011

Related U.S. Application Data

(60) Provisional application No. 61/015,383, filed on Dec. 20, 2007.

(51) Int. Cl.
*A61M 15/00* (2006.01)
(52) U.S. Cl.
CPC ....... *A61M 15/0065* (2013.01); *A61M 15/0025* (2014.02); *A61M 15/0045* (2013.01); *A61M 15/0048* (2014.02); *A61M 2202/064* (2013.01); *A61M 2206/10* (2013.01)
(58) Field of Classification Search
USPC ............. 128/203.12, 203.15, 203.19, 203.22, 128/200.24
See application file for complete search history.

(56) References Cited

U.S. PATENT DOCUMENTS

| 2,214,032 A * | 9/1940 | Stewart ............... 128/203.15 |
| 3,872,970 A | 3/1975 | Edison |
| 3,948,264 A | 4/1976 | Wilke et al. |
| 4,210,140 A | 7/1980 | James et al. |
| 4,446,862 A | 5/1984 | Baum et al. |

(Continued)

FOREIGN PATENT DOCUMENTS

| AU | 651910 | 3/1993 |
| CN | 1867369 A | 11/2006 |

(Continued)

OTHER PUBLICATIONS

PCT International Search Report, mailed on Nov. 3, 2009, in PCT/SE2008/051490 (6 pages).

(Continued)

*Primary Examiner* — Jason Flick
*Assistant Examiner* — Eric Bryant
(74) *Attorney, Agent, or Firm* — Finnegan, Henderson, Farabow, Garrett & Dunner LLP.

(57) ABSTRACT

The present disclosure relates to a method for entraining in an airflow a medicament powder contained in a cavity having a cavity opening. Large airflow vortices are provided, for instance, by use of an obstacle in a flow passage, The airflow with large vortices is arranged to by-pass the cavity opening, thereby generating an eddy in the cavity which contributes to entraining the powder in said airflow. The present disclosure also relates to a medical dispenser, for instance an inhaler, in which the method may be performed.

16 Claims, 15 Drawing Sheets

(56) References Cited

U.S. PATENT DOCUMENTS

| | | | |
|---|---|---|---|
| 4,849,606 A | 7/1989 | Martens, III et al. | |
| 4,860,740 A | 8/1989 | Kirk et al. | |
| 4,946,038 A | 8/1990 | Eaton | |
| 5,042,472 A * | 8/1991 | Bunin | |
| 5,383,850 A | 1/1995 | Schwab et al. | |
| 5,437,271 A * | 8/1995 | Hodson et al. | 128/203.15 |
| 5,469,843 A | 11/1995 | Hodson | |
| 5,590,645 A | 1/1997 | Davies et al. | |
| 5,660,169 A * | 8/1997 | Kallstrand et al. | 128/203.15 |
| 5,676,130 A * | 10/1997 | Gupte et al. | 128/203.19 |
| 5,694,920 A | 12/1997 | Abrams et al. | |
| 5,699,789 A * | 12/1997 | Hendricks | 128/203.15 |
| 5,724,959 A * | 3/1998 | McAughey et al. | 128/203.15 |
| 6,006,747 A | 12/1999 | Eisele et al. | |
| 6,102,035 A | 8/2000 | Asking et al. | |
| 6,234,169 B1 | 5/2001 | Bulbrook et al. | |
| 6,286,507 B1 * | 9/2001 | Jahnsson | 128/203.15 |
| 6,328,034 B1 | 12/2001 | Eisele et al. | |
| 6,575,160 B1 * | 6/2003 | Volgyesi | 128/203.15 |
| 6,637,431 B2 | 10/2003 | Ekelius et al. | |
| 6,655,381 B2 | 12/2003 | Keane et al. | |
| 6,840,239 B2 | 1/2005 | Myrman | |
| 6,871,647 B2 | 3/2005 | Allan et al. | |
| 6,923,178 B2 * | 8/2005 | Snow | 128/203.15 |
| 6,948,494 B1 | 9/2005 | Snow | |
| 6,971,383 B2 * | 12/2005 | Hickey et al. | 128/203.15 |
| 7,395,821 B2 | 7/2008 | Lulla et al. | |
| 7,448,379 B2 | 11/2008 | Yamashita et al. | |
| 7,533,668 B1 * | 5/2009 | Widerstrom | 128/203.15 |
| 7,810,495 B2 | 10/2010 | Gumaste | |
| 8,151,793 B2 | 4/2012 | Lastow et al. | |
| 8,479,729 B2 | 7/2013 | Lastow et al. | |
| 8,578,933 B2 | 11/2013 | Remmelgas et al. | |
| 2001/0027790 A1 | 10/2001 | Gleschen et al. | |
| 2003/0015195 A1 | 1/2003 | Haaije de Boer et al. | |
| 2003/0192539 A1 * | 10/2003 | Myrman | 128/203.15 |
| 2004/0069303 A1 | 4/2004 | Brown et al. | |
| 2004/0107963 A1 | 6/2004 | Finlay et al. | |
| 2004/0123864 A1 | 7/2004 | Hickey et al. | |
| 2005/0076924 A1 * | 4/2005 | Dobak, III | 128/898 |
| 2006/0150969 A1 * | 7/2006 | Connelly et al. | 128/200.14 |
| 2006/0237010 A1 | 10/2006 | De Boer et al. | |
| 2007/0131576 A1 | 6/2007 | Ehling et al. | |
| 2007/0137645 A1 | 6/2007 | Eason et al. | |
| 2007/0151562 A1 | 7/2007 | Jones et al. | |
| 2007/0181123 A1 | 8/2007 | Houzego | |
| 2008/0001008 A1 | 1/2008 | Thoemmes et al. | |
| 2008/0023367 A1 * | 1/2008 | Lastow | 206/539 |
| 2008/0127974 A1 | 6/2008 | Lastow | |
| 2008/0142076 A1 | 6/2008 | Bulbrook | |
| 2008/0314384 A1 | 12/2008 | Harris et al. | |
| 2009/0013994 A1 | 1/2009 | Jones et al. | |
| 2009/0084379 A1 | 4/2009 | Goeckner et al. | |
| 2009/0114220 A1 | 5/2009 | Wachtel et al. | |
| 2010/0000529 A1 | 1/2010 | Prime et al. | |
| 2010/0051027 A1 | 3/2010 | Remmelgas et al. | |
| 2010/0300442 A1 | 12/2010 | Houzego et al. | |
| 2011/0036348 A1 | 2/2011 | Lastow et al. | |
| 2011/0226243 A1 | 9/2011 | Lastow et al. | |
| 2012/0298106 A1 | 11/2012 | Kjellgren et al. | |
| 2014/0000601 A1 | 1/2014 | Arvidsson et al. | |
| 2014/0083422 A1 | 3/2014 | Arvidsson et al. | |
| 2014/0096771 A1 | 4/2014 | Remmelgas et al. | |

FOREIGN PATENT DOCUMENTS

| | | |
|---|---|---|
| DE | 1 769 818 B1 | 11/2009 |
| EP | 0 938 907 A1 | 9/1999 |
| EP | 1 106 196 A2 | 6/2001 |
| EP | 1 173 368 B1 | 6/2005 |
| EP | 1 844 806 A1 | 10/2007 |
| EP | 1 318 849 B1 | 4/2009 |
| EP | 1 769 818 B1 | 11/2009 |
| GB | 1 472 650 | 5/1977 |
| GB | 1 502 150 | 2/1978 |
| GB | 1 520 062 | 8/1978 |
| GB | 1 521 000 | 8/1978 |
| GB | 2 264 237 A | 8/1993 |
| GB | 2 401 548 A | 11/2004 |
| WO | WO 9204069 A1 | 3/1992 |
| WO | WO 97/25086 A2 | 7/1997 |
| WO | WO 98/34663 A1 | 8/1998 |
| WO | WO 99/36116 A1 | 7/1999 |
| WO | WO 0053248 A1 | 9/2000 |
| WO | WO 0064779 A1 | 11/2000 |
| WO | WO 03/051839 A1 | 6/2003 |
| WO | WO 03/103563 A2 | 12/2003 |
| WO | WO 2005/030305 A1 | 4/2005 |
| WO | WO 2005/081977 A2 | 9/2005 |
| WO | WO 2006/026754 A2 | 3/2006 |
| WO | WO 2006/118527 A1 | 11/2006 |
| WO | WO 2007/144614 A1 | 12/2007 |
| WO | WO 2008/008021 A1 | 1/2008 |
| WO | WO 2008/010765 A1 | 1/2008 |
| WO | WO 2008/110809 A2 | 9/2008 |
| WO | WO 2009/008832 A1 | 1/2009 |
| WO | WO 2009/082341 A1 | 7/2009 |
| WO | WO 2009/093969 A1 | 7/2009 |
| WO | WO 2009/152477 A2 | 12/2009 |
| WO | WO 2010/042035 A1 | 4/2010 |
| WO | WO 2010/042036 A1 | 4/2010 |
| WO | WO 2011/002406 A1 | 1/2011 |

OTHER PUBLICATIONS

PCT Written Opinion of the International Searching Authority, mailed on Nov. 3, 2009, in PCT/SE2008/051490 (7 pages).

PCT International Preliminary Report on Patentability, issued on Jun. 22, 2010, in PCT/SE2008/051490 (8 pages).

Atvars, K. et al., "Experimental and Computational Investigation of an 'Open' Transonic Cavity Flow" *Proceedings of the Institution of Mechanical Engineers, Part G: Journal of Aerospace Engineering* 223(4):357-368 (Apr. 1, 2009).

International Search Report and Written Opinion issued in International Patent Application No. PCT/SE2008/051488; Date of Mailing: Mar. 10, 2009.

Ukeiley, L. et al., "Velocity and surface pressure measurements in an open cavity" *Experiments in Fluids* 38:656-671 (2005).

Zhang, X., "Compressible Cavity Flow Oscillation due to Shear Layer Instabilities and Pressure Feedback" *AIAA Journal* 33(8):1404-1411 (Aug. 1995).

U.S. Appl. No. 12/940,683, filed Nov. 5, 2010 by Lastow et al.: Notice of Allowance, dated Dec. 9, 2011.

U.S. Appl. No. 12/940,683, filed Nov. 5, 2010 by Lastow et al.: Office Action, dated Jul. 15, 2011.

U.S. Appl. No. 12/940,683, filed Nov. 5, 2010 by Lastow et al.: Office Action, dated May 26, 2011.

English abstract of German Patent Publication No. DE 102005046645 B3 [online]. Retrieved from Espacenet, http://worldwide.espacenet.com, published by the European Patent Office; updated Mar. 13, 2013 (2 pages).

International Search Report issued in International Patent Application No. PCT/GB2011/051349; Date of Mailing: Feb. 3. 2012.

International Search Report issued in International Patent Application No. PCT/GB2011/051350; Date of Mailing: Nov. 2, 2011.

International Search Report and Written Opinion issued in International Patent Application No. PCT/SE2010/050749; Date of Mailing: Oct. 4, 2010.

* cited by examiner

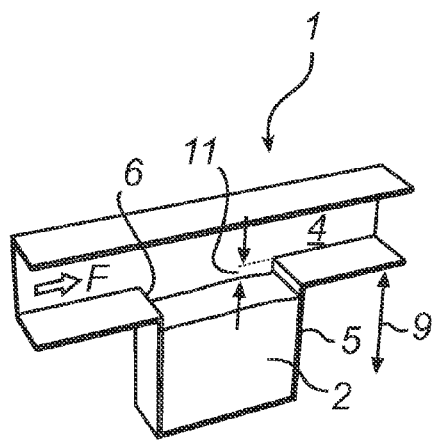
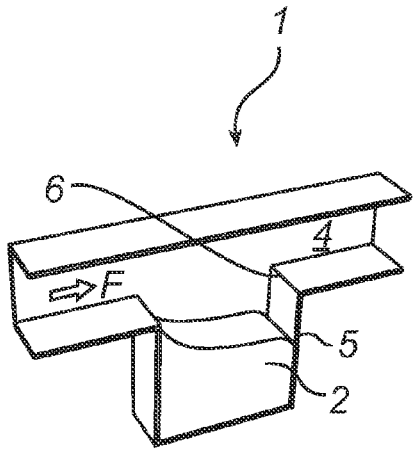
Fig. 5a        Fig. 5b
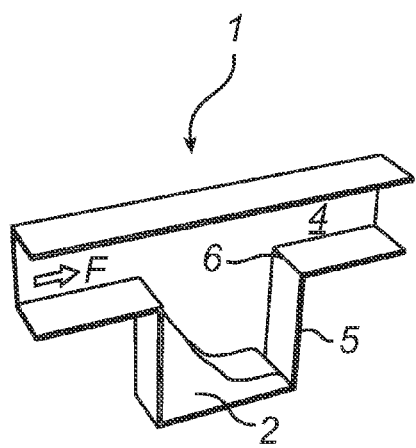
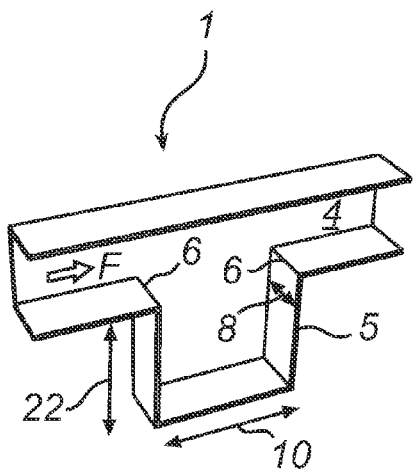
Fig. 5c        Fig. 5d

DISPENSER AND METHOD FOR ENTRAINING POWDER IN AN AIRFLOW

This is a U.S. National Phase Application of PCT/SE2008/051490, filed Dec. 18, 2008, which claims the benefit of priority to U.S. Provisional Application No. 61/015,383, filed Dec. 20, 2007, both of which are incorporated herein by reference in their entireties.

TECHNICAL FIELD

The present invention relates to a method for entraining in an airflow a medicament powder contained in a cavity. The present invention also relates to a medical dispenser, comprising a powder-containing cavity.

BACKGROUND OF THE INVENTION

There are many devices for administering powdered medicaments to the lungs, which employ propellants, such as compressed gases, e.g. air, or liquefied gas propellants, to dispense and disperse the medicament. There are also a number of known breath actuated inhalation devices for administering powdered medicaments to the lungs, which have mouthpieces through which the medicament is inhaled. British Patent Specification Nos. 1 521 000, 1 520 062, 1 472 650 and 1 502 150 disclose more complex devices in which a complete capsule is inserted into the device thus ensuring no spillage of medicament prior to inhalation, and access to the medicament is gained by piercing the capsule or cutting it in half, inside the dispensing device. On inhalation the air flows into or through the capsule and the powder within is released into the air stream and flows towards the mouth.

U.S. Pat. No. 4,210,140 discloses a device in which access to the powdered medicament is gained by pulling the halves of the capsule apart so that the medicament is emptied to a suitable position for entrainment in the airflow caused by inhalation.

U.S. Pat. No. 6,655,381 relates to a pre-metered dose assembly for consistently supplying precise doses of medicament for a breath-actuated dry powder inhaler. The assembly includes a cap defining a dry powder delivery passageway for providing air to a dry powder supply port of a swirl chamber of a breath-actuated dry powder inhaler, and a magazine including a plurality of reservoirs for holding pre-metered doses of dry powder. One of the magazine and the cap is movable with respect to the other of the magazine and the cap for sequentially positioning the reservoirs within the delivery passageway of the cap. A breath-induced low pressure at an outlet port of the inhaler causes an air flow through the dry powder delivery passageway of the assembly and into the dry powder supply port that entrains dry powder from the reservoir positioned in the passageway for inhalation by a patient using the inhaler. The passageway is provided with a venturi in the passageway by the reservoir to create a flow through the reservoir and bring the powder there from.

In spite of the numerous prior art devices it would be desirable to provide a simple yet efficient administering of powdered medicaments into the alveolar region of the lungs. Indeed, it would be desirable to be enable the medicament powder to be efficiently deaggregated before being administered into the alveolar region of the lungs. In addition to the above mentioned methods of enabling deaggregation in the prior art, there exist various ways of enabling deaggregation by vibrating, shaking or providing alternative obstacles in the flow passage etc. It is common to strive for a deaggregation that makes a significant amount of the powder particles to be in accordance with a desired size and weight. This is often referred to as classifying of the powder particles. These prior art deaggregation devices may result in contamination of the downstream flow passage since medicament powder may accumulate in the downstream region of the device e.g. by certain alternative obstacles. It is of course desirable to reduce or avoid the risk of administering an inaccurate amount of medicament powder. Thus, a general reduction of powder retention within the device is desirable.

SUMMARY OF THE INVENTION

The above-mentioned object is achieved by providing a method and a dispenser as defined in the accompanied claims.

The present invention is based on the insight that the build-up of an eddy in a powder-containing cavity may contribute to entraining the powder into a by-passing airflow. The invention is also based on the insight that, the built-up eddy contributes to deaggregating the powder within the cavity. It has been found that such an eddy may be generated by the actual by-passing airflow. The invention is further based on the insight that the entrainment benefits from providing one or more eddies presenting a three-dimensional direction of rotation rather than a substantially two-dimensional direction of rotation. It has been found that such an eddy or eddies which jump back and forth in the cavity are obtainable by, upstream of the cavity, controlling the flow pattern of the airflow by-passing the cavity. In particular, it has been found that an airflow which by-passes the cavity opening and which has a flow pattern presenting relatively large vortices (compared to a flow pattern presenting relatively small or no vortices) generates an eddy in the cavity which results in a comparatively increased entrainment of powder from the cavity.

Although there is no semantic difference between the terms "vortex" and "eddy" or "vortices" and "eddies", in this application, in order to avoid confusion, the terms "vortex" and "vortices" are used when describing the motion of the air outside the cavity, while the terms "eddy" and "eddies" are used when describing the motion of air inside the cavity.

According to a first aspect of the invention, there is provided a method for entraining in an airflow a medicament powder contained in a cavity having a cavity opening. The method comprises providing an airflow to be passed outside the cavity along the cavity opening, the provided airflow initially having a first flow pattern, changing, upstream of the cavity opening, said provided first flow pattern into a second flow pattern having larger vortices than the first flow pattern, and passing, along the cavity opening, the airflow having said second flow pattern, thereby generating an eddy in the cavity which contributes to entraining the powder in said airflow.

An eddy may be created in the cavity with an airflow having no or relatively small vortices, such an airflow may be regarded as having, on average, a rather symmetrical velocity profile and flow pattern. An eddy created by such an airflow will have a mainly two-dimensional direction of rotation, i.e. the geometrical axis round which the eddy rotates will mainly be confined to one direction. Said geometrical axis will typically extend perpendicular to the direction of the by-passing airflow, but be confined to a plane parallel with the direction of the by-passing airflow.

However, by providing a by-passing airflow having relatively large vortices (the airflow may be regarded as having an asymmetrical velocity profile and flow pattern) the turbulent airflow will affect the generated eddy by moving it back and forth in the cavity. Thus, the eddy will become inclined at various angles when the extension of the geometrical axis of the eddy will change between several directions. This eddy will be likely to reach more portions of the cavity and thereby increase the amount of powder entrained in the by-passing airflow compared to the above described eddy which has a geometrical axis mainly extending in one direction.

According to at least one example embodiment of the invention, the change into said second flow pattern (having larger vortices than said first flow pattern) is accomplished by means of an obstacle arranged in the flow path upstream of the cavity. The airflow is caused to pass round the obstacle. The obstacle may be in the form of a solid object, such as having the form of a polyhedron formed by triangular, rectangular and/or other polygonal faces. Alternatively, the obstacle may have curved or rounded faces such as in the form of a cylinder. Other forms, such as U-shapes, V-shapes, etc. are also conceivable. Although the obstacle may be centred with respect to the main direction of flow, it may alternatively be located off-centre. The upstream location of the cavity may be both far away from or near the cavity, as long as the second flow pattern with the large vortices is able to be formed and maintained when passing over the cavity. Perpendicular to the main flow direction, the obstacle may, for instance, have a cross-sectional area which is about 5-25% of the cross-sectional area of the flow passage, suitably about 5-20%, such as about 5-15%.

Although the obstacle may be substantially unaffected by the passing airflow and thus remain stationary, it may be arranged and shaped as a compliant body or be made of a compliant material so that the airflow causes the obstacle to flutter, which in turn may create vibrations in the airflow.

The first initial flow pattern may comprise some small vortices and in such case it does not represent a real laminar flow. Nevertheless, the obstacle will cause an identifiable change of the flow pattern. There will be larger vortices downstream of the obstacle and the velocity profile will be more asymmetric than upstream of the obstacle. Thus, the obstacle may be regarded as a turbulence promoter and/or an asymmetry-creating (or symmetry-breaking) object in the flow passage. Furthermore, since an obstacle provided upstream of the cavity changes the behaviour of the eddy in the cavity (compared to the case when no obstacle is present), the obstacle may also be regarded as an eddy-controlling feature.

From above, it should now be clear that an airflow, having said second flow pattern and by-passing the cavity opening, will have a positive effect on the entrainment of powder from the cavity into the by-passing airflow. This is due to the wobbling eddy reaching into large parts of the cavity. However, for an airflow which is directed as a jet into the cavity, rather than directed in parallel with the rim defining the cavity opening, it would not make much difference whether said jet has said first flow pattern or said second flow pattern. This is because, contrary to the effect that a by-passing airflow has on the generated eddy in the cavity, in the case of a jet directed into the cavity, the jet itself would have the main emptying effect, and any turbulence would play just a small part of it.

According to at least one example embodiment, the velocity of the airflow and the size and shape of the obstacle are configured to generate von Kármán vortices downstream of the obstacle. The von Kármán vortices have been found to generate a fluctuating eddy which affects a large area within the cavity, thereby enabling more powder to be entrained from the cavity than when a substantially two-dimensional eddy-movement is present in the cavity. The friction of the obstacle causes the airflow to slow down, thereby increasing the pressure. The von Kármán vortices are formed in the wake created downstream of the obstacle at Reynolds (Re) number greater than 47, Re=Vd/v, where V=steady velocity of the flow upstream of the obstacle; d=diameter of the obstacle (or some other suitable measure of width of non-circular bodies); and v=the kinematic viscosity of the airflow. A further discussion of von Kármán vortices may be found in Marcel Lesieur, *Turbulence in Fluids—Stochastic and Numerical modelling*. (1990). Kluwer Academic Publishers, Dordrecht, The Netherlands.

According to at least one example embodiment of the invention, the method comprises directing the airflow having said second flow pattern such that its main flow direction is substantially parallel with the plane coinciding with a rim defining the cavity opening. Thus, although the airflow may in alternative embodiments by-pass, the cavity at an angle to the cavity rim plane, e.g. depending on the configuration of the rim, a parallel flow has been found to provide suitable entrainment of the powder within the cavity. This is what creates a shear driven cavity flow. More in detail, the airflow may be given the desired parallel direction by suitable design of flow passage-defining wall portions, such that the flow passage directs the airflow in said parallel manner. Suitably, the sides of the cavity pass perpendicularly into the flat surface region.

According to at least one example embodiment, the method comprises directing the airflow having said first flow pattern at an inclination relative to the plane coinciding with the rim defining the cavity opening, and performing said change into said second flow pattern before the airflow is directed substantially in parallel with said plane. In other words, there may be provided a slope or a bevelled surface which is provided upstream of and angled relative to the plane of the rim. In the case when said change is effected by means of said obstacle, the obstacle may suitably be provided at that slope or bevelled surface, as it may facilitate the assembly process of a dispenser in which the method is performed. In particular, in production, when the powder is introduced into the cavity of the dispenser, the obstacle may be less in the way, e.g. if a scrape is used to provide the powder into the cavity. Of course, it is also conceivable to provide the obstacle at the flat surface region which may coincide with the plane of the rim.

According to at least one example embodiment the angle of said inclination is about 30°-60° relative to the plane coinciding with the rim defining the cavity opening.

The method according to the first aspect of the invention may suitably be implemented in a medical dispenser, e.g. an inhaler, a nebulizer, a respirator or other medical device in which a powder is to be entrained in an airflow.

Thus, according to a second aspect of the invention, a medical dispenser is provided. The medical dispenser comprises a powder-containing cavity, a flow passage comprising a flat surface region located both upstream and downstream of the cavity, said flat surface region comprising an opening into said cavity, the opening being defined by a rim, wherein the flat surface region lies in the plane coinciding with the rim or in a plane parallel with the plane coinciding with the rim, and an obstacle provided in the flow passage upstream of the cavity causing an airflow to pass round the obstacle.

According to at least one example embodiment, said obstacle projects from a flow passage-defining wall portion.

As previously discussed, the obstacle may suitably be provided on a slope or bevelled portion. This is reflected in at least one example embodiment, according to which said flow passage-defining wall portion is provided upstream of and passing into said flat surface region and is inclined with respect to said flat surface region.

The medical dispenser may be a single dose dispenser or a multidose dispenser. Thus, according to at least one example embodiment, said powder-containing cavity is one of a plurality of powder-containing cavities having individual flow passages, and wherein said obstacle is one of a plurality of obstacles, each obstacle being associated with a respective flow passage. An alternative would be to use a single obstacle which is movable to be aligned with the flow passage and cavity from which the next dose is to be dispensed.

According to at least one example embodiment, said flow passage-defining wall portion is inclined with respect to said flat surface region at an angle of about 30°-60°.

According to at least one example embodiment, the medical dispenser is in the form of an inhaler comprising a mouthpiece or nasal adapter through which medicament powder contained in said cavity is inhalable.

According to at least one example embodiment, the medical dispenser comprises a cavity structure holder for a cavity structure having a plurality of cavities containing respective doses of powder. The cavity structure holder forms part of at least one of the wall portions of the flow passage. The shape of the flow passage allows for a simple design which in turn allows for use of less elements leading to facilitated manufacturing process. Suitably, said plurality of cavities are integrally formed in said cavity structure.

According to at least one example embodiment, the medical dispenser comprises a seal component, which is releasably covering said cavity opening in a pre-inhaling condition. Suitably, the seal component of the cavity opening is releasable upon breath actuation.

It should be understood that the second aspect of the invention encompasses any embodiments or any features described in connection with the first aspect of the invention, as long as those embodiments or features are compatible with the medical dispenser of the second aspect.

The medical dispenser, when provided in the form of an inhaler, may contain various drugs and/or bioactive agents to be inhaled.

The bioactive agent may be selected from any therapeutic or diagnostic agent. For example it may be from the group of antiallergics, bronchodilators, bronchoconstrictors, pulmonary lung surfactants, analgesics, antibiotics, leukotriene inhibitors or antagonists, anticholinergics, mast cell inhibitors, antihistamines, antiinflammatories, antineoplastics, anesthetics, anti-tuberculars, imaging agents, cardiovascular agents, enzymes, steroids, genetic material, viral vectors, antisense agents, proteins, peptides and combinations thereof.

Examples of specific drugs which can be incorporated in the medical dispenser according to the invention include mometasone, ipratropium bromide, tiotropium and salts thereof, salmeterol, fluticasone propionate, beclomethasone dipropionate, reproterol, clenbuterol, rofleponide and salts, nedocromil, sodium chromoglycate, flunisolide, budesonide, formoterol fumarate dihydrate, Symbicort™ (budesonide and formoterol), terbutaline, terbutaline sulphate, salbutamol base and sulphate, fenoterol, 3-[2-(4-Hydroxy-2-oxo-3H-1, 3-benzothiazol-7-yl)ethylamino]-N-[2-[2-(4-methylphenyl) ethoxy]ethyl]propanesulphonamide, hydrochloride. All of the above compounds can be in free base form or as pharmaceutically acceptable salts as known in the art.

Combinations of drugs may also be employed, for example formoterol/budesonide; formoterol/fluticasone; formoterol/mometasone; salmeterol/fluticasone; formoterol/tiotropium salts; zafirlukast/formoterol, zafirlukast/budesonide; montelukast/formoterol; montelukast/budesonide; loratadine/montelukast and loratadine/zafirlukast.

Further combinations include tiotropium and fluticasone, tiotropium and budesonide, tiotropium and mometasone, mometasone and salmeterol, formoterol and rofleponide, salmeterol and budesonide, salmeterol and rofleponide, and tiotropium and rofleponide.

BRIEF DESCRIPTION OF THE DRAWINGS

FIGS. 5a-5d schematically illustrate, by means of a schematic perspective view in cross section, an inhalation sequence.

FIG. 9b shows a cross section along line b-b in FIG. 9a.

FIG. 9c shows a cross section along line c-c in FIG. 9a.

DETAILED DESCRIPTION OF THE DRAWINGS

Figure 1:
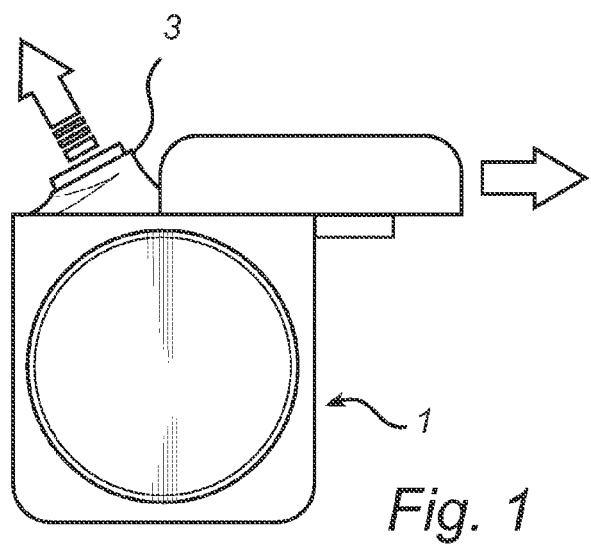
FIG. 1 illustrates an inhaler according to an example embodiment of the invention.

FIG. 1 illustrates an inhaler 1 according to an example embodiment of the invention. A user may inhale consecutive doses of medicament in the form of dry powder. Although the illustrated device is a multidose inhaler, the general inventive concept is also applicable to and encompasses a single dose inhaler. The inhaler 1 includes a housing and a mouthpiece 3. The mouthpiece 3 may be uncovered by linear movement of the mouthpiece cover. The mouthpiece cover according to another example embodiment is pivotally supported by the housing of the inhaler 1.

Figure 6A:
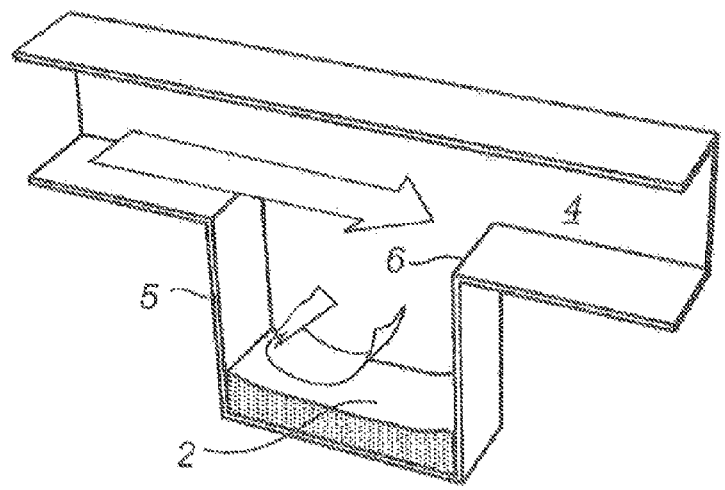
FIG. 6a is a schematic illustration of an eddy generated in a cavity in an inhaler.
Figure 6B:
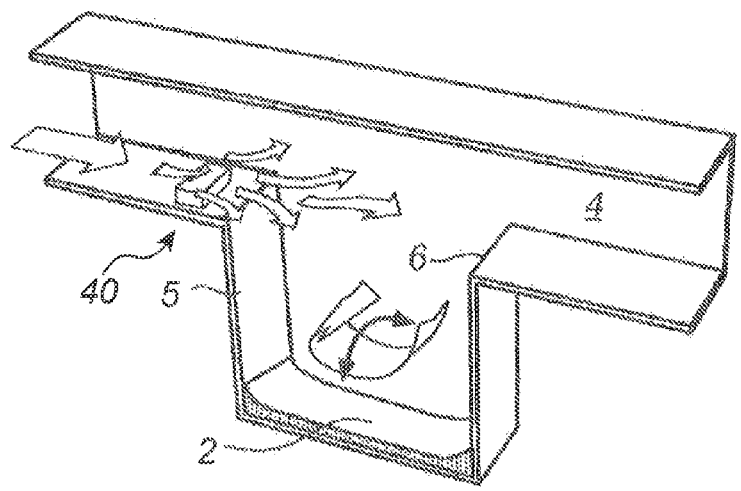
FIG. 6b is a schematic illustration of an eddy generated in a cavity in an inhaler, wherein an obstacle is provided upstream of the cavity.

The inventive idea of changing, upstream of the cavity opening, a first flow pattern into a second flow pattern having larger vortices than the first flow pattern, will be discussed in connection with FIGS. 6a-6b and onwards. As an introduction to that discussion, with reference to FIGS. 2-5, there will first be presented an inventive idea of using a shear driven cavity principle in an inhaler, wherein an airflow by-passing a cavity generates an eddy in the cavity for deaggregation and entrainment of the powder contained in the cavity.

Figure 2:
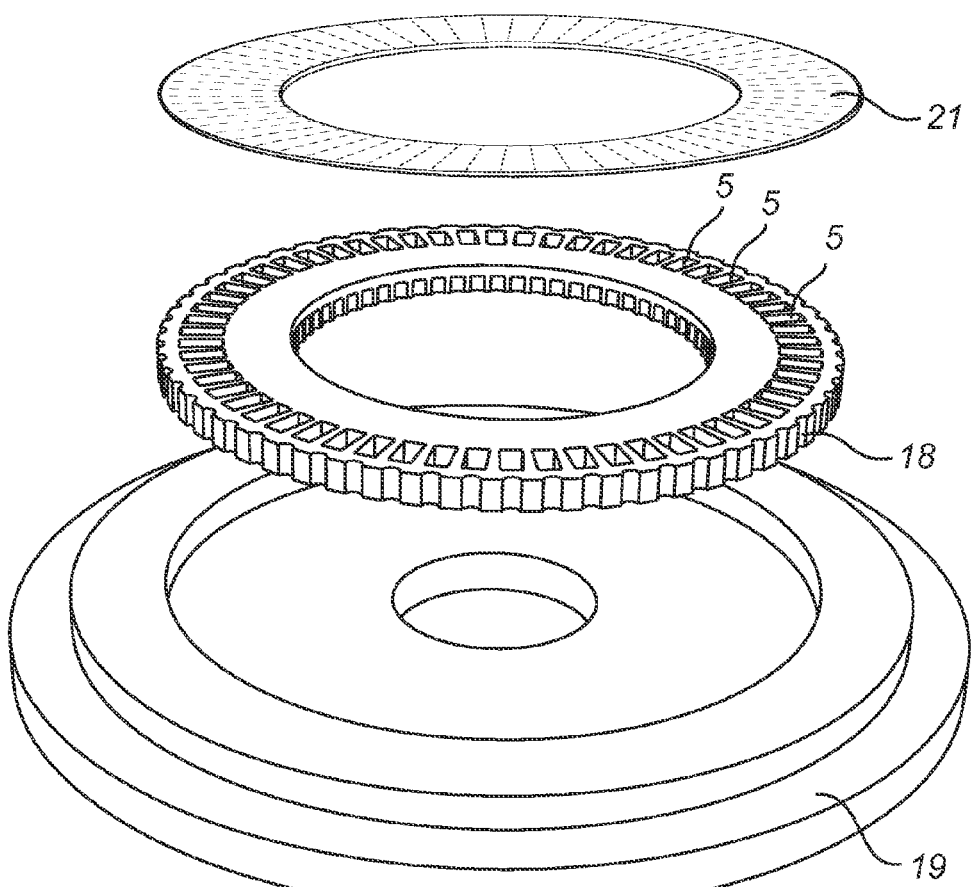
FIG. 2 illustrates an exploded partial view of some schematic general details in an inhaler.

FIG. 2 illustrates an exploded partial view of some schematic general details in an inhaler. Inside the housing of the inhaler there is provided a cavity structure 18 containing a plurality of cavities 5. In accordance with the illustrated example, the cavity structure 18 is positioned in a cavity structure holder 19. The cavity structure 18 is suitably provided with a plurality of cavities 5 in an annular pattern. Moreover, the cavity structure 18 in accordance with the illustrated example is annular with a comparatively large hole in the centre thereof. A seal component 21, herein illustrated as an annular foil is attached to the cavity structure 18 to seal the cavities 5 containing the powder. Removal of a portion of the seal component 21 above a cavity 5 enables an inhalation airflow to entrain the powder contained in the cavity.

Figure 3:
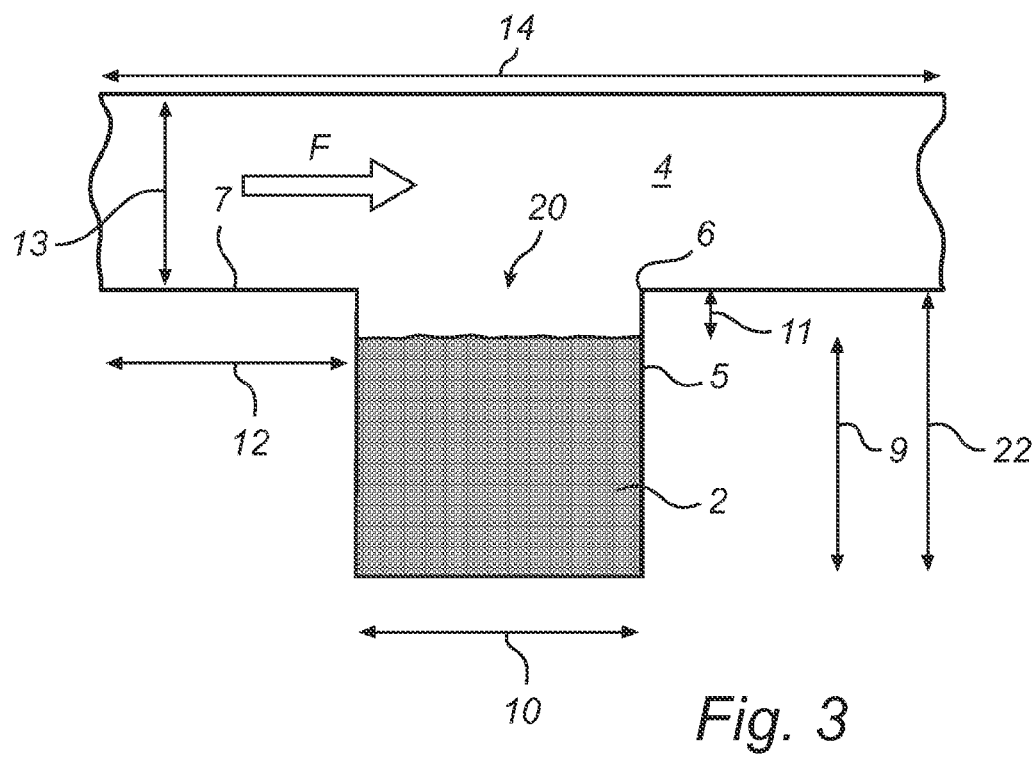
FIG. 3 is a schematic cross sectional view of a flow passage region at a cavity in an inhaler.

FIG. 3 is a schematic cross sectional view of a flow passage region at a cavity 5 in an inhaler. The cavity 5 is brick-shaped and the cavity opening has a rim 6 where the sides of the cavity 5 change into the flow passage flat surface region 7. In the cavity 5, an eddy is developing efficiently when it describes a circular movement pattern. It is advantageous that the cavity/cavities 5 in question is/are shaped to allow a cylindrical wind flow pattern within the cavity 5. The cylindrical flow pattern in the cavity would be developed around an axis located transverse the flow direction and in the middle of the cavity when the device is held in normal operation condition. Suitably, the sides of the cavity transforms perpendicularly into the flat surface region 7 of the cavity structure 18 which in turn is aligned with the flat surface of the cavity structure holder 19 providing for an appropriate flow direction in the flow passage (not shown in FIG. 2).

Part of the flow passage 4 propagates along a flat surface region 7. The flat surface region 7, which forms the bottom of the flow passage 4 when the inhaler is in its intended use condition, comprises a cavity opening 20 into said powder-containing cavity 5. The passing of an airflow in the main flow direction (F) along said flat surface region 7 and outside said cavity 5 generates an eddy in the cavity 5 and the generated eddy contributes to deaggregation of the powder 2 in said cavity 5. The powder particles are brought against the sides within the cavity 5 when the shear driven cavity eddy is generated. When the powder particles hit the sides of the cavity 5 they become deaggregated and thus appropriate for administration. Furthermore, the generated eddy contributes to the emptying of the powder 2 from said cavity 5.

More in particular the cavity 5 and cavity opening 20 each have a length 10 in the main flow direction (F) of the flow passage 4 which is in the range of 65% to 135% of the cavity depth 22. More suitable, the cavity 5 and cavity opening 20 each have a length 10 in the main flow direction (F) of the flow passage which is in the range of 85% to 115% of the cavity depth 22 and more preferably in the range of 95% to 105% of the cavity depth 22 of said cavity 5. More in detail one cavity side, when taken in a cross section of the cavity as seen from above when the device is in the normal use condition and the opening of the cavity is facing upwards, has a width 8 in the propagating direction of the flow passage 4 which is in the range of 35% to 135% of the length 10 of the cavity 5, preferably in the range of 45% to 115% of the length 10 of the cavity 5, and more preferably in the range of 50% to 100% of the length 10 of the cavity 5.

Suitably, the distance from the top of the cavity 5 to the top of the powder particle bed in an initial condition is 1 mm or more than 1 mm. This distance is referred to as the headspace 11 of the cavity. The cavity 5 is provided with a headspace 11 between powder top and the cavity rim 6; the headspace 11 is at least 1 mm. A headspace ranging in between 1-3 mm would be suitably but depends also on the total cavity depth. Possibly, the headspace may vary in between 10 to 80% of the cavity depth provided that the shape of the cavity is adapted for deaggregation as described above. It is also found that the mass flow rate of the device 1 is fairly insensitive to the depth 22 of the cavity, at least following an initial induction period of approximately 5-10 ms. The extent of the headspace 11 is suitably between 10 and 35% of the cavity depth 22 and the cavity depth 22, from rim 6 to bottom of a brick-shaped cavity 5, is between 4 and 10 mm.

Consequently, a suitable cross sectional shape of the cavity 5, as seen from the side, is a quadratic shape. The inner corners of the cavity are essentially sharp. The edges 16, 17 of the cavity 5 that propagates transverse to the air stream direction and are present in the bottom of the cavity 5 may have a slightly curved shape (not shown in FIG. 3) in order to provide some guidance in the rotational movement of the generated eddy.

Figure 4:
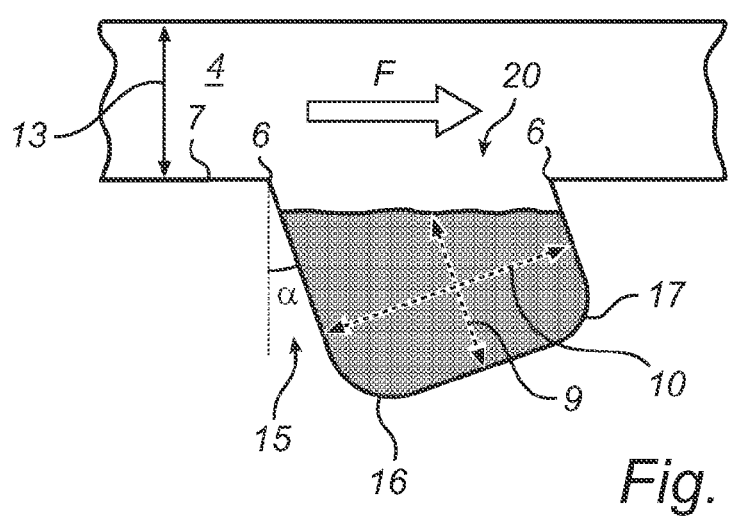
FIG. 4 is a schematic cross sectional view of a flow passage region at a cavity having an alternative configuration.

FIG. 4 is a schematic cross sectional view of a flow passage region at a cavity having an alternative configuration. The sides of the cavity 5 are positioned with an angle ($\alpha$) in relation to a normal direction to the main flow direction (F). The rim 6 of the cavity opening 20 will still be aligned with a plane parallel to the main flow direction (F) of the airflow in the flow passage 4 by the cavity 5. The inclination of the side walls in relation to the flow passage 4 will make it more difficult for the generated eddy to provide for dispensing of powder from the cavity 5. Hence, a design in accordance with this alternative will increase the time during which the medicament powder 2 is subject to wall contact impact and hence the deaggregation time period may be extended. On the other hand the emptying time will, in analogy with the above explained also be longer for this alternative compared to a similar type but with a design in accordance with FIG. 3. It is also found that the flow in the device is qualitatively similar for most flow rates.

Continuing with reference to FIG. 4 and the shape of the cavity 5, suitably, the bottom most edges 16, 17, of a substantially brick shaped cavity, located in the transverse direction in relation to the flow direction (F) may have a curved shape. The first edge 17 in the more downstream position in relation to the second edge 16 has a shorter radius than said second edge 16. The first arrow 9 indicates how the cavity powder depth is measured. The headspace 11 is the distance between the top of the dry powder and the rim 6 of the cavity 5. The length 10 of the cavity is also illustrated in FIG. 4 with an arrow carrying reference number 10.

FIGS. 5*a*-5*d* schematically illustrate, by means of a schematic perspective view in cross section, a inhalation sequence. The illustrated design of the device provides for use of a phenomenon denoted as shear driven cavity principle during deaggregation of the powder 2 in the cavity 5 and emptying operation of the powder 2 there from. Suitably, the flow passage 4 is arranged to follow a generally horizontal line from upstream to downstream of the cavity. The flow passage 4 is arranged to guide the airflow passing the opening 20 of the cavity 5 on the outside of the cavity opening 20 thereof.

In FIG. 5*a* it is disclosed a cavity 5 which is filled with powder 2 with a suitable headspace 11. An airflow along the flow passage 4 is initiated in the flow direction (F) and emptying of the cavity 5 starts. Moving to FIG. 5*b*, in which some of the powder 2 has left the cavity 5, the build up of an eddy air stream in the cavity 5 has begun and it is seen that the cavity 5 is emptied in the downstream region and further upstream when moving to FIG. 5*c*. The time period elapsed from the situation in FIG. 5*a* to that in FIG. 5*d* when the emptying of the cavity 5 is completed depends of course on the size and magnitude of flow, depth, powder composition, powder depth, headspace etc. In at least one example embodiment the emptying time including deaggregation is from 30 ms. For instance, the emptying time including deaggregation may be 500 ms.

The shear driven cavity is a model for flow in a cavity 5 where the upper boundary moves in a desired flow direction (F), and thus causes a rotation of gas/air in the cavity 5. The flow occurs at a Reynolds number which is likely higher than 4000 so the upper boundary flow may be assumed to be turbulent in general cases. The patterns during this process are quite complex. The opposing side surfaces of the flow passage 4 are arranged with a broadening propagation in relation to one another in the flow direction. To mention an example, a device comprising a disc in accordance with the illustration in FIG. 2 which has 60 cavities will have side walls of the flow passage which broadens at an angle of 4 degrees in relation to a centerline of the flow passage. In an alternative embodiment in which the disc is provided with 30 cavities the side walls of the flow passage broadens at an angle of 12 degrees in relation to a centerline of the flow passage. The flow passage 4 may be formed with a constant distance between upper and lower flat surface region in the upstream region in relation to the cavity 5. Furthermore, the flow passage 4 in the downstream region in relation to the cavity 5 may be formed with the same distance as the upstream region. The cross sectional shape of the flow passage 4 in the cavity region is also formed in the same manner. The cross sectional shape of the flow passage 4 is suitably substantially rectangular with dimensions ranging between 1 to 5 mm. The shear driven cavity flow principle may also be implemented in a single inhalation device containing one cavity with medicament powder.

Rectangular cavities 5 are attractive provided they have an appropriate depth. For these cavities, the emptying time and the wall deposition factor is predicted to increase as the depth increases. The deaggregation potential is predicted to decrease as the depth increases beyond 5 mm, but a local maximum is found for depths near 4 mm.

An inspection of the flow behavior suggests that deaggregation is promoted by devices for which $\alpha>0$ because the cavity 5 affects the air stream in such a way that the powder 2 particles that are about to escape from the cavity are more likely to re-enter the cavity. The particles that fail to escape from the cavity 5 instead impact on the downstream wall of the cavity 5, which causes deaggregation. Since particles are less likely to escape the cavity for devices with $\alpha>0$, the emptying time is longer.

For illustrative and explanatory purposes, FIGS. 5*a*-5*d* have shown a complete emptying of the powder from the cavity, however, in reality there generally remains some amount of powder in the cavity after a user has inhaled. In connection with the following drawings, some example embodiments will be described which reduce the powder retention in the cavity.

In connection with FIGS. 6*a*-6*b* and onwards, there will now be discussed the inventive idea of changing, upstream of the cavity opening, a first flow pattern into a second flow pattern having larger vortices than the first flow pattern.

FIG. 6*a* is a schematic illustration of an eddy generated in a cavity in an inhaler. The powder is entrained in the same manner as illustrated in FIGS. 5*a*-5*d*. Thus, an airflow (straight arrow) passes substantially linearly through the flow passage 4. The main direction of the airflow is substantially parallel to the plane defined by the rim 6 of the cavity 5. As the airflow by-passes the cavity 5 it affects the layer of air present in the cavity 5, and consequently an eddy (curved arrow) is generated in the cavity 5. The generated eddy rotates around a geometrical axis which is substantially pointing in one direction across the cavity 5, namely perpendicular to the main flow direction and in a plane parallel with the plane defined by the rim 6 of cavity 5. In other words said geometrical axis extends along the width of the cavity 5.

FIG. 6*b* is a schematic illustration of an eddy generated in a cavity 5 in an inhaler, wherein an obstacle 40 is provided upstream of the cavity 5. This figure illustrates that an obstacle 40 will affect the airflow in the flow passage 4. Before reaching the obstacle 40, i.e. upstream of the obstacle 40, the airflow has a first flow pattern, which substantially corresponds to the flow pattern in the case illustrated in FIG. 6*a*. The first flow pattern has no or relatively small vortices. This is illustrated with a linear broad arrow. However, when the airflow reaches the obstacle 40, it forces the airflow to pass around the obstacle 40, thereby changing the airflow into a second flow pattern which has relatively large vortices. This is illustrated by a plurality of small arrows in various directions and curvatures. Downstream of the obstacle 40, the airflow now having the second flow pattern, will still have a main flow direction along the flow passage 4 as the airflow by-passes the cavity 5. Thus, it will similarly to the case illustrated in FIG. 6*a* generate an eddy in the cavity 5. However, since the second flow pattern in the case illustrated in FIG. 6*b* has larger vortices and is more asymmetric, the eddy will wobble. This is illustrated with the double-headed arrow. Thus, the geometrical axis around with the eddy rotates will change directions. This means that a larger part, such as corner portions, of the cavity will be reached by the wobbling eddy (FIG. 6*b*) compared to what is reached by a relatively stationary eddy (FIG. 6*a*). As a result of the wobbling eddy reaching a larger part of the cavity 5, the retention of powder will be less, as schematically illustrated in FIG. 6*b*. It should be noted that FIGS. 6*a* and 6*b* have merely been provided schematically illustrate and explain an inventive principle.

FIG. 7 illustrates a perspective partial view of a cavity structure 118 usable in at least one example embodiment of the invention. Compared with the cavity structure 18 illustrated in FIG. 2, the cavity structure 118 in FIG. 7 has at the inner periphery a different design. Upstream of each cavity 105, there is provided a respective slope 130. The slope 130 rises from the inner periphery and reaches its top at a flat surface region 107 located downstream of the slope 130 but upstream of the cavity 105. The flat surface region 107 lies in the plane of the rim 106 defining the cavity opening 120. The plurality of slopes 130 are separated by intermediate vertical side walls 132 forming part of flow passage-defining wall portions. From each slope 130 a respective obstacle 140 projects upward in a direction towards the plane of the rim 106 defining the cavity opening 120. In this example embodiment the obstacle 140 has the shape of a polyhedron having a substantially triangular cross section. The top surface of the obstacle 140 lies in a plane which is parallel or coincides with the flat surface region 107.

It should be understood that FIG. 7 is merely an example embodiment and that there are many other alternative embodiments. For instance, the cavity structure may be formed without slopes (such as in FIG. 2) so that each obstacle would project from the flat surface region upstream of the cavity (such as in FIG. 6*b*). Likewise, the shape of the obstacle may be another type of polyhedron or even a rounded shape, and the height and width of the obstacle may also vary.

In the following, a comparison will be made between the velocity profile in a flow passage region at a cavity 105, with and without an obstacle 140 being present upstream of the cavity 105. FIG. 8*a* illustrates a velocity profile in a flow passage region at a cavity 105 in an inhaler. The drawing shows a view taken from above the cavity 105. Denser areas represent higher airflow velocity than less dense areas. As may be seen, the velocity profile is substantially symmetrical along the main flow direction in a plane parallel to the plane defined by the rim of the cavity opening.

Figure 8A:
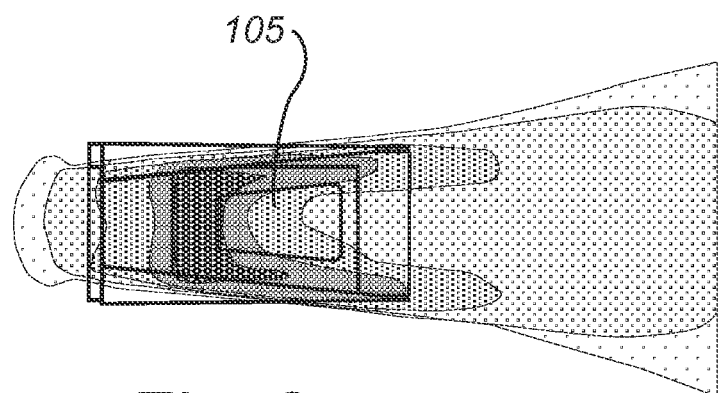
FIG. 8a illustrates a velocity profile in a flow passage region at a cavity in an inhaler.
Figure 8B:
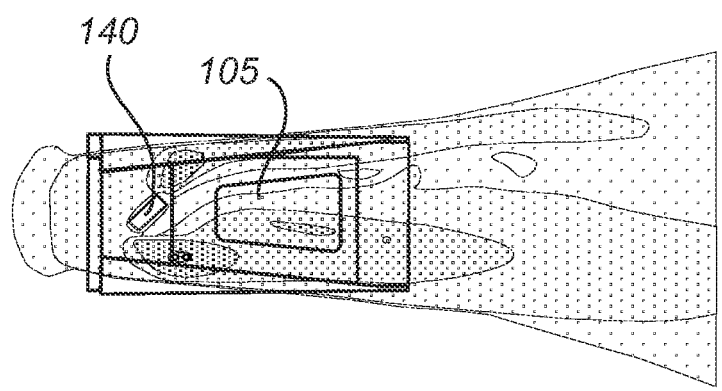
FIG. 8b illustrates a velocity profile in a flow passage region at a cavity in an inhaler, wherein an obstacle is provided upstream of the cavity.

FIG. 8b illustrates a velocity profile in a flow passage region at a cavity 105 in an inhaler, wherein an obstacle 140 is provided upstream of the cavity 105. The velocity profile in this case is more asymmetric compared to the velocity profile shown in FIG. 8a. This asymmetric velocity profile is an indication of larger vortices being present in the airflow by-passing the cavity 105 than if no obstacle is present upstream of the cavity 105. Thus, the provision of the obstacle has an impact on the velocity profile and the flow pattern. Upstream of the obstacle 140, any vortices are relatively small, while downstream of the obstacle the vortices are relatively large.

As mentioned under the summary of the invention, by providing a by-passing airflow having relatively large vortices the turbulent airflow will affect the eddy generated in the cavity by moving it back and forth in the cavity. Thus, the eddy will become inclined at various angles when the extension of the geometrical axis of the eddy will change between several directions. This eddy will be likely to reach more portions of the cavity and thereby increase the amount of powder entrained in the by-passing airflow compared to the eddy described in connection with FIGS. 5a-5d, which has a geometrical axis extending mainly in one direction.

Figure 9A:
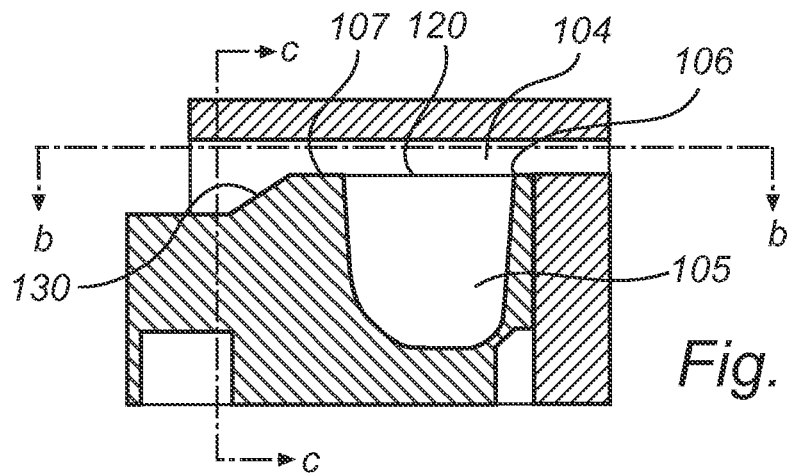
FIG. 9a is a schematic cross sectional view of a flow passage region in which a slope changes into a flat surface region in a plane coinciding with the rim defining the cavity opening.
Figure 9B:
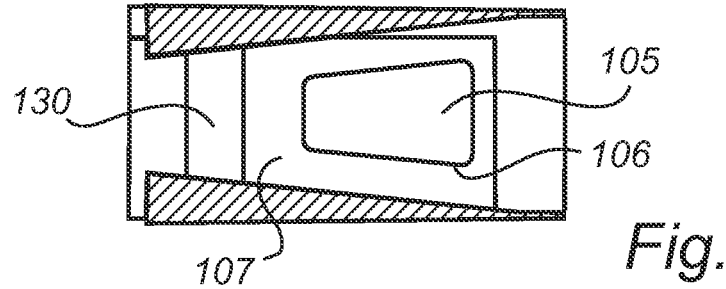
Figure 9C:
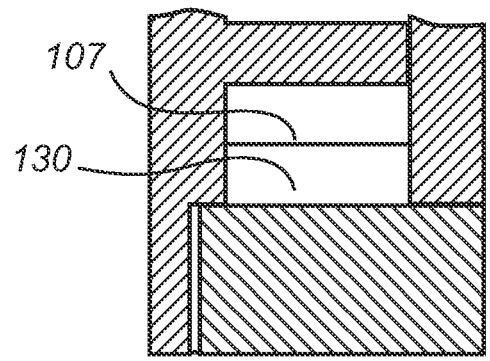

In the following the retention of powder in the cavity 105 will be discussed for flow passages 104 provided with different obstacles (FIGS. 10a-10c to 17a-17c) and compared with a flow passage 104 without an obstacle (FIGS. 9a-9c). In each case a cavity 105 was provided with 14-16 mg of a powder composition comprising lactose and budesonide (5%). The doses were withdrawn at 1.5 kPa (approximately 40 lpm). The suction volume was 4 litres.

Starting with FIG. 9a, there is shown a schematic cross sectional view of a flow passage region in which a slope 130 changes into a flat surface region 107 in a plane coinciding with the rim 106 defining the cavity opening 120. FIG. 9b shows a cross section along line b-b in FIG. 9a, and FIG. 9c shows a cross section along line c-c in FIG. 9a. Upstream of the cavity 105, there is no obstacle for changing a flow pattern of an airflow having small vortices to a flow pattern of an airflow having large vortices. The cavity retention, i.e. the amount of powder remaining in the cavity after the dose had been withdrawn as specified above, was 10% of the total dose.

FIGS. 10a-10c to 17a-17c illustrate various examples of obstacles in the flow passage region which may be used in example embodiments of the invention. The views correspond to those shown in FIGS. 9a-9c.

Figure 7:
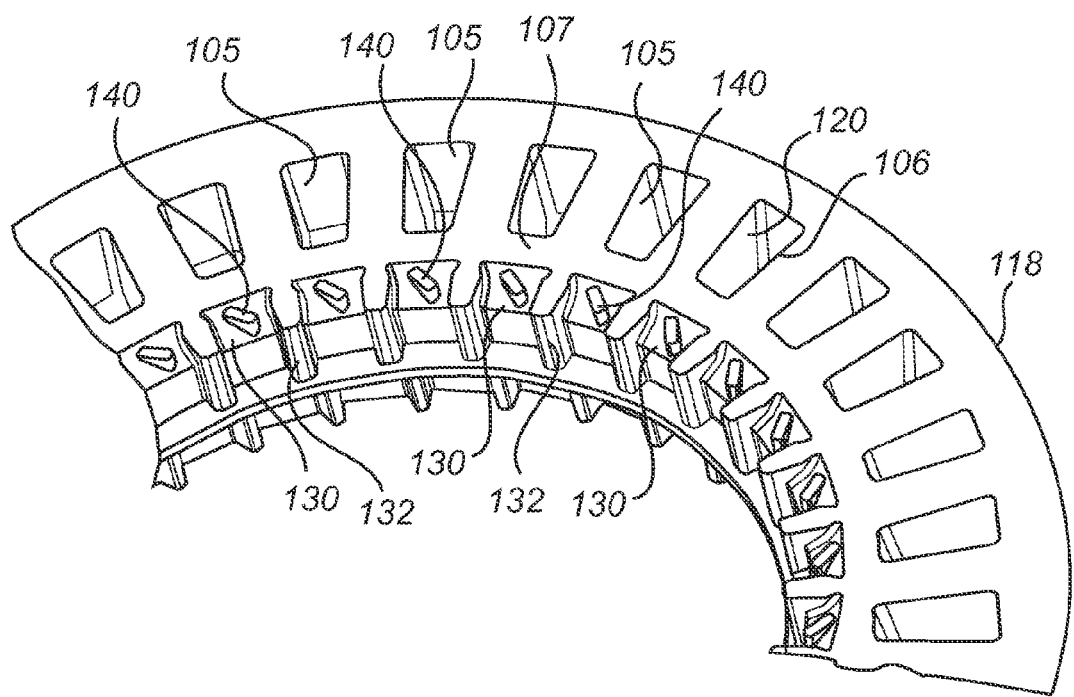
FIG. 7 illustrates a perspective partial view of a cavity structure usable in at least one example embodiment of the invention.
Figure 10A:
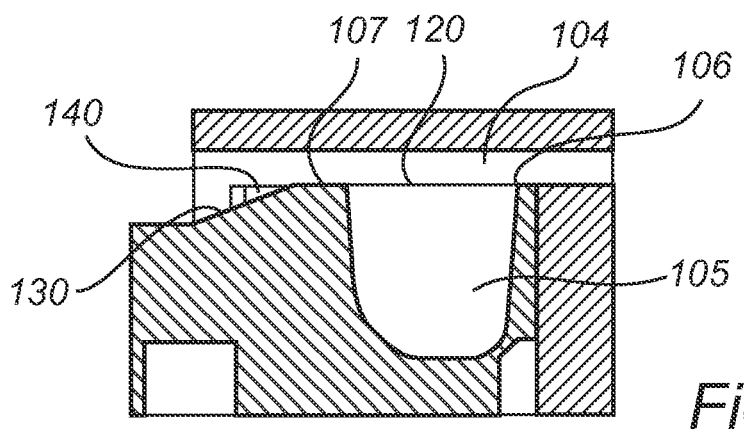
FIGS. 10a-10c to 17a-17c illustrate various examples of obstacles in the flow passage region which may be used in example embodiments of the invention. The views correspond to those shown in FIGS. 9a-9c.
Figure 10B:
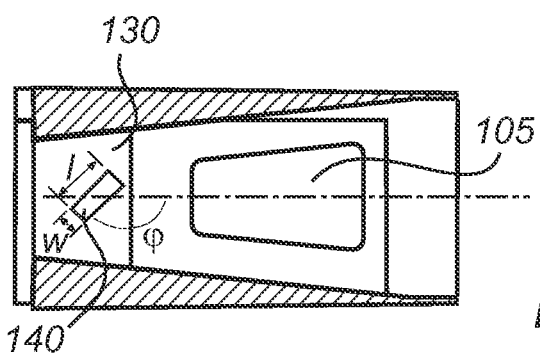
Figure 10C:
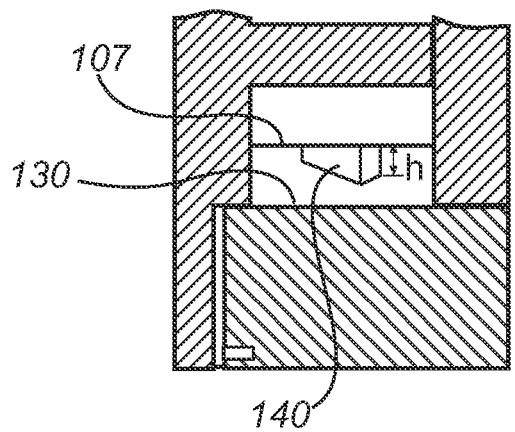

In FIGS. 10a-10c an obstacle 140 is present and corresponds to the example embodiment illustrated in FIG. 7. The highest part of the obstacle 140 relative to the slope 130 projects to a height (h) of about 0.6 mm from the surface of the slope 130. The top surface of the obstacle is level with the plane of the flat surface region 107 and the rim 106 defining the cavity opening 120. The long side of the obstacle 140 has a length (l) of about 0.85 mm. The short side of the obstacle 140 has a width (w) of about 0.5 mm. The obstacle 140 is turned with its long side at angle ($\phi$) of about 135° to the central geometrical axis of the flow passage 104. As can be seen from the drawings the flow passage 104 widens in the downstream direction. Thus, the relative cross-sectional area of the obstacle 140 compared to the cross-sectional area of the flow passage 104 will vary in the flow direction. However, on average, perpendicular to the main flow direction the cross-sectional area of the obstacle 140 is about 5.2% of the cross-sectional area of the flow passage 104. The smallest distance between the obstacle 140 and the cavity 105 is about 1.69 mm in this example. The cavity 105 retention was 5%. In other words, the is presence of the obstacle 140 reduces the amount of powder remaining in the cavity 105 after inhalation to half the amount compared to the case when no obstacle is present (as in FIGS. 9a-9c).

Figure 11A:
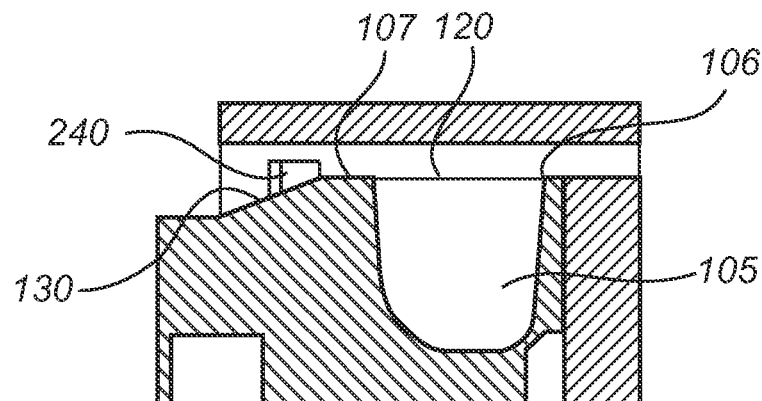
Figure 11B:
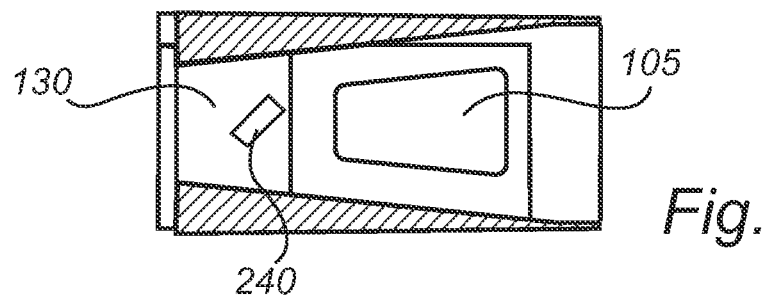
Figure 11C:
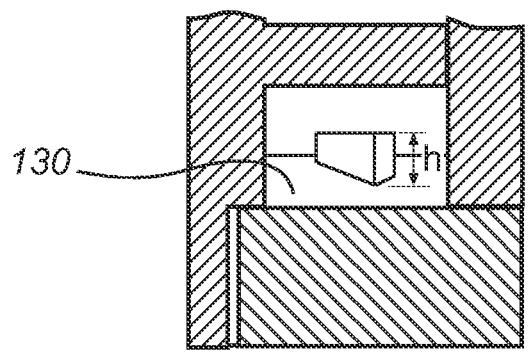

FIGS. 11a-11c show an obstacle 240 which is similar to the one shown in FIGS. 10a-10c, for instance, having the same length (l), width (w) and angle ($\phi$). However, the highest part of the obstacle relative to the slope 130 projects to a height (h) of about 1 mm from the surface of the slope 130. Therefore, the top surface of the obstacle 240 lies about 0.4 mm above the plane of the flat surface region 107 and the rim 106 defining the cavity opening 120. Furthermore, perpendicular to the main flow direction the average cross-sectional area of the obstacle 240 is about 10.7% of the cross-sectional area of the flow passage. The smallest distance between the obstacle 240 and the cavity 105 is about 1.19 mm in this example. The cavity retention was only 3%.

Figure 12A:
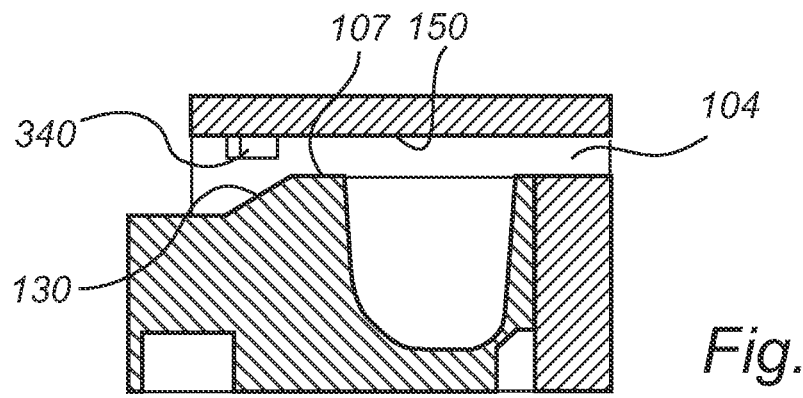
Figure 12B:
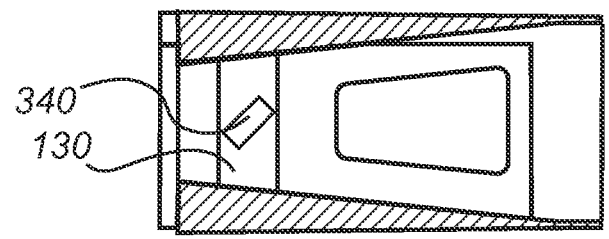
Figure 12C:
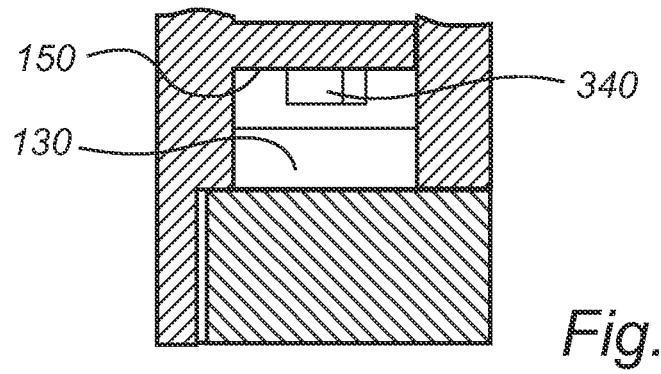

FIGS. 12a-12c show an obstacle 340 which has similar dimensions to the one shown in FIGS. 10a-10c, for instance having the same length (l), width (w) and angle ($\phi$), however it projects downwards about 0.6 mm from a roof portion 150 of the inhaler above the slope 130. Thus, the obstacle 340 is spaced from the slope 130. The roof portion 150 contributes to define the flow passage 104. Perpendicular to the main flow direction the average cross-sectional area of the obstacle 340 is about 8.1% of the cross-sectional area of the flow passage 104. The cavity retention was 5%.

Figure 13A:
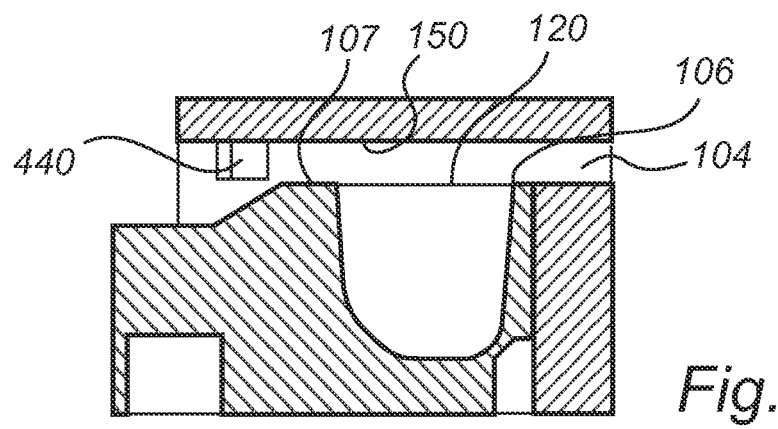
Figure 13B:
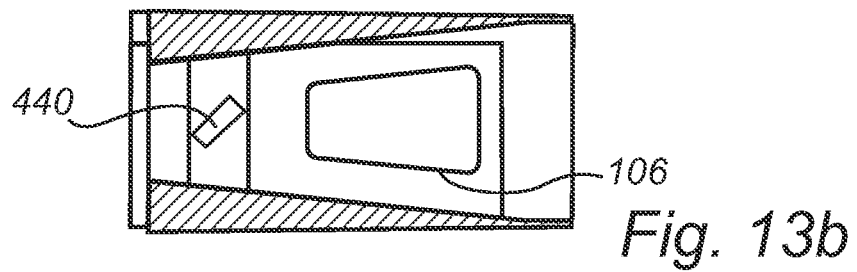
Figure 13C:
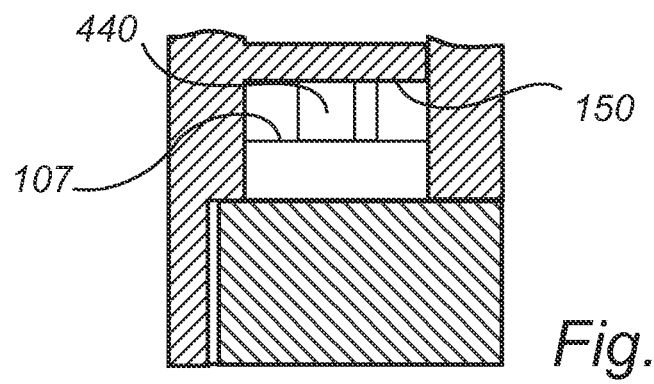

FIGS. 13a-13c show an obstacle 440 which has similar dimensions to the one shown in FIGS. 12a-12c, for instance having the same length (l), width (w) and angle ($\phi$), however it projects downwards about 1 mm from the roof portion 150. The bottom surface of the obstacle is substantially level with the plane of the flat surface region 107 and the rim 106 defining the cavity opening 120. Perpendicular to the main flow direction the average cross-sectional area of the obstacle 440 is about 13.5% of the cross-sectional area of the flow passage 104. The cavity retention was 4%.

Figure 14A:
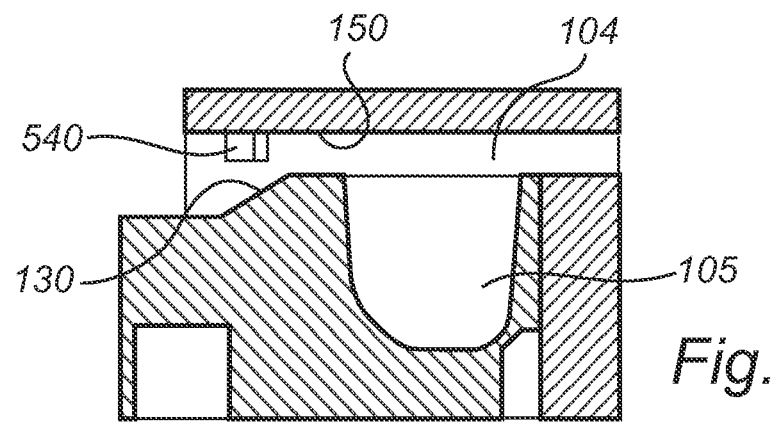
Figure 14B:
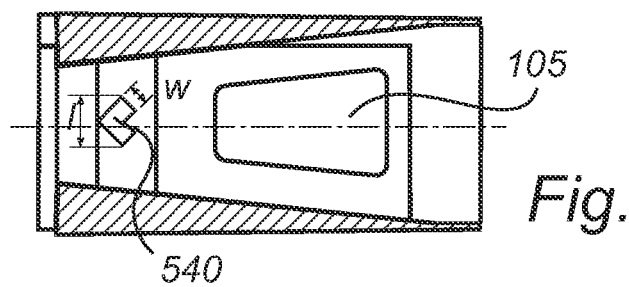
Figure 14C:
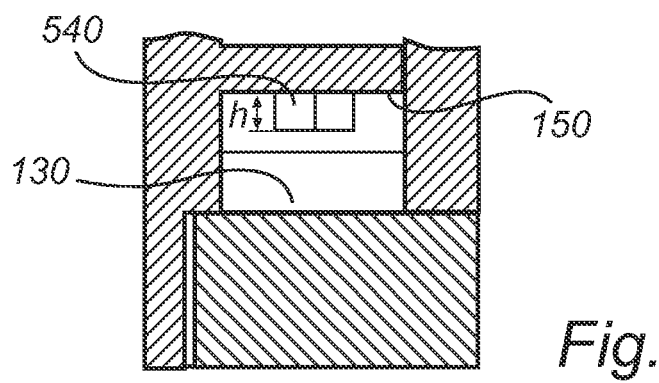

FIGS. 14a-14c show an obstacle 540 which is symmetrically about the central geometrical axis of the flow passage and which projects from the roof portion 150. The obstacle 540 is shaped as a right-angled bracket with legs projecting at 90° relative each other and meeting each other at the upstream end of the obstacle. The width (w) of each leg is about 0.5 mm and the longest extension (l) of the obstacle 540 across the flow path is about 1.3 mm. The height (h) of the obstacle is 0.6 mm. At the longest extension (l) of the obstacle 540, the flow passage has a width of about 3.39 mm and a height from roof portion 150 to slope 130 of about 1.57 mm. Thus, perpendicular to the main flow direction the cross-sectional area of the obstacle 540 is about 14.7% ((1.3*0.6)/(3.39*1.57)) of the cross-sectional area of the flow passage 104. The distance between cavity 105 and obstacle 540 is about 2 mm. The cavity retention was 7%.

Figure 15A:
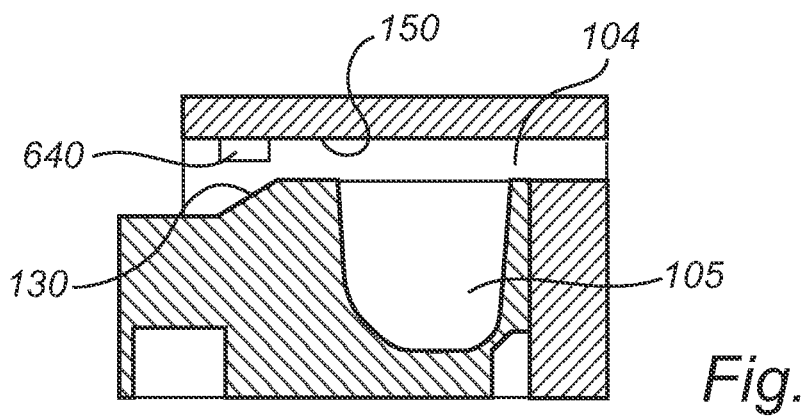
Figure 15B:
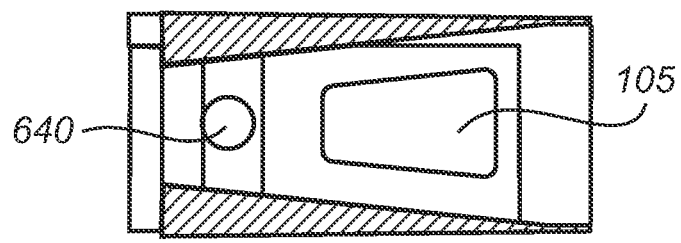
Figure 15C:
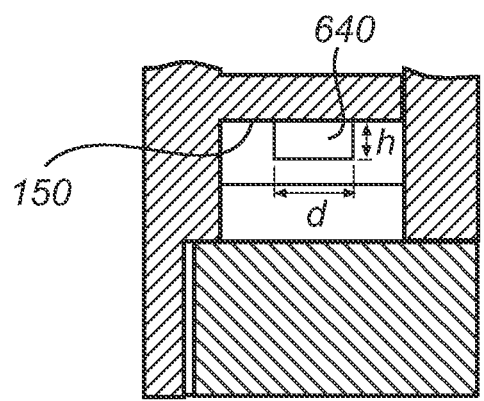

FIGS. 15a-15c show an obstacle 640 in the form of a cylinder which projects from the roof portion 150. The height (h) of the cylinder is 0.6 mm and the diameter (d) is 1.3 mm. Thus, as for the angled obstacle 540 in FIGS. 14a-14c, perpendicular to the main flow direction, the cylindrical obstacle 640 covers about 14.7% of the cross sectional area of the flow passage 104. The distance between the cavity 105 and the obstacle 640 is about 1.7 mm. The cavity retention was 4%.

Figure 16A:
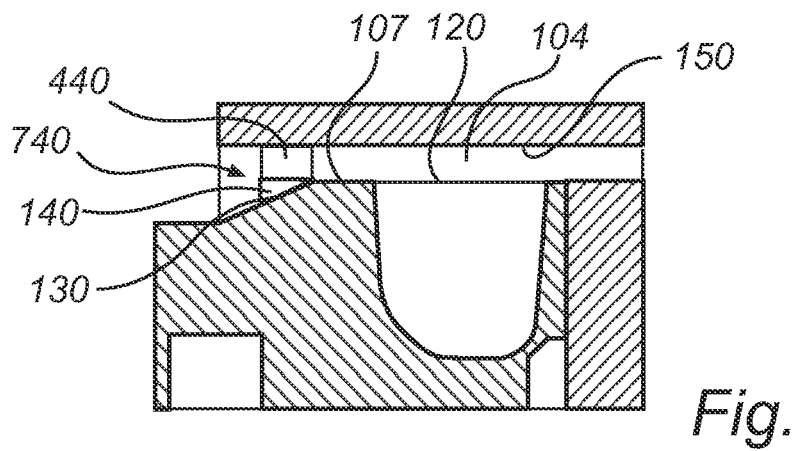
Figure 16B:
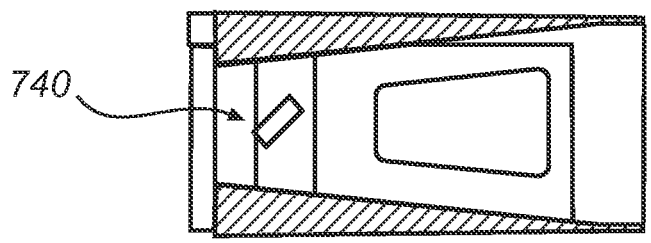
Figure 16C:
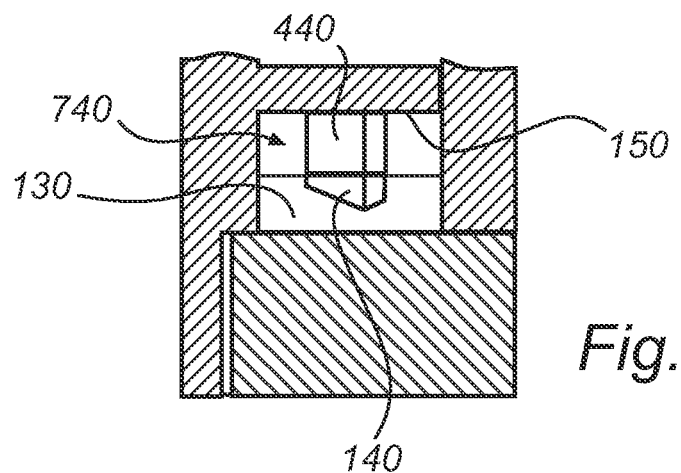

FIGS. 16a-16c show a two-part obstacle 740 which is substantially a combination of the obstacle 140 shown in FIGS. 10a-10c and the obstacle 440 shown in FIGS. 13a-13c.

Thus, the two-part obstacle 740 extends substantially all the way from the slope 130 to the roof portion 150. Perpendicular to the main flow direction the average cross-sectional area of the two-part obstacle 740 is about 20.9% of the cross-sectional area of the flow passage 104. The cavity retention was 6%.

Figure 17A:
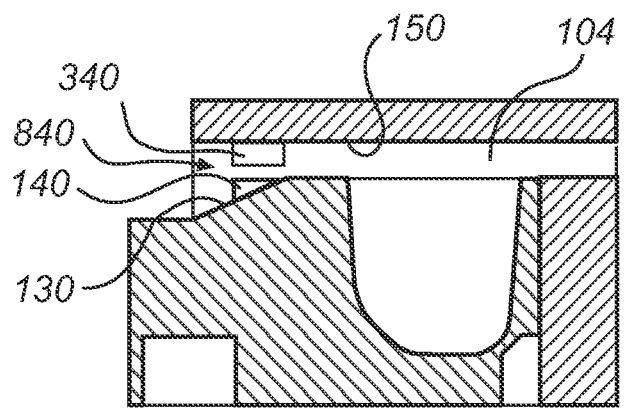
Figure 17B:
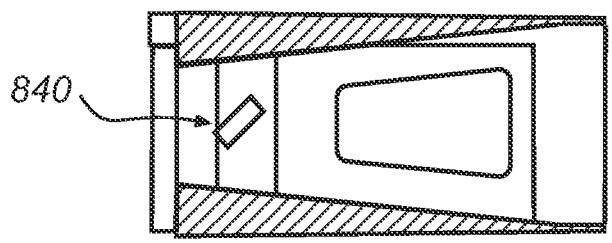
Figure 17C:
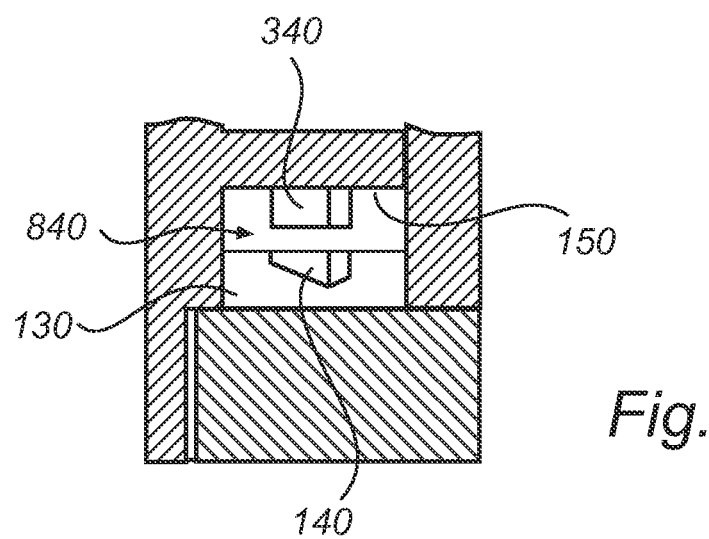

FIGS. 17*a*-17*c* show a two-part obstacle 840 which is substantially a combination of the obstacle 140 shown in FIGS. 10*a*-10*c* and the obstacle 340 shown in FIGS. 12*a*-12*c*. Thus, the one part 140 of the obstacle projects the slope 130 and another part 340 of the obstacle projects from the roof portion 150, wherein there is a gap between the two parts. Perpendicular to the main flow direction the average cross-sectional area of the two-part obstacle 840 is about 14.6% of the cross-sectional area of the flow passage 104. The cavity retention was 6%.

It is realised that the features of the above presented embodiments is not a complete description of all aspects of the invention and further combinations of features from different embodiments are conceivable within the claimed scope of protection. Hence, it is possible to combine various features with different embodiments within the claimed scope for enabling further aspects of the invention. Furthermore, the various features in the drawings have primarily been illustrated for explanatory purposes, and are thus not necessarily drawn to scale.

The invention claimed is:

1. A method for entraining in an airflow, flowing through a passageway having a longitudinal axis, a medicament powder contained in a cavity having a cavity opening in fluid communication with the passageway, wherein the passageway includes a lower surface region containing the cavity opening and an obstacle, which is fixed and rigid, located upstream of the cavity opening, and an upper surface region extending continuously parallel to the longitudinal axis from upstream of the obstacle to downstream of the cavity and located opposite the lower surface region, comprising:

providing an airflow to be passed generally parallel to the longitudinal axis between the upper surface region and the lower surface region and outside the cavity along the cavity opening, the provided airflow initially having a first flow pattern;

changing, upstream of the cavity opening, the first flow pattern into a second flow pattern having larger vortices than the first flow pattern; and passing, along the cavity opening, the airflow having said second flow pattern, thereby generating an eddy in the cavity which contributes to entraining the medicament powder in said airflow to provide less than about 10% retention of, medicament powder within the cavity, wherein the cavity always remains stationary relative to the passageway.

2. The method of claim 1, further including:

directing the airflow having said second flow pattern such that a main flow direction is substantially parallel with a plane coinciding with a rim defining the cavity opening.

3. The method as claimed in claim 2, further including:

directing the airflow having said first flow pattern at an inclination relative to the plane coinciding with the rim defining the cavity opening; and changing the first flow pattern into the second flow pattern before the airflow is directed substantially in parallel with said plane.

4. A medical dispenser, comprising:

a powder containing cavity;

a flow passage comprising a flat surface region, which is generally flat, located upstream of the cavity, wherein the powder containing cavity is fixedly and rigidly coupled to the flat surface region and the flat surface region comprises an opening from the flow passage into the powder containing cavity; and an obstacle located in the flow passage upstream of the powder containing cavity and not extending into the powder containing cavity, wherein the obstacle is configured to cause an airflow to pass around and over the obstacle and the obstacle is fixedly and rigidly coupled to and extends from a flow passage-defining wall portion that is positioned upstream of and at an incline with respect to said flat surface region.

5. The method of claim 1, wherein the eddy moves generally laterally within the cavity.

6. The method of claim 5, wherein the eddy wobbles within the cavity.

7. The medical dispenser of claim 4, wherein the opening has a leading edge, a trailing edge, and two diverging side edges.

8. The medical dispenser of claim 4, wherein the obstacle has a longitudinal axis positioned at an angle relative to a longitudinal axis of the flow passage.

9. The medical dispenser of claim 4, wherein the obstacle has a substantially triangular cross section.

10. The medical dispenser of claim 4, wherein the flow passage includes a longitudinal axis, and the powder containing cavity and the obstacles are positioned along the longitudinal axis.

11. The medical dispenser of claim 4, wherein the flow passage and the powder containing cavity both include side walls extending downstream that at least partially diverge in a downstream direction.

12. The medical dispenser of claim 4, wherein the obstacle includes a cross section extending parallel to the flat surface region that is rectangular.

13. The medical dispenser of claim 4, wherein the obstacle includes a top surface extending parallel to the flat surface region.

14. The medical dispenser of claim 13, wherein the top surface is in a plane coincident with the flat surface region.

15. The medical dispenser of claim 4, wherein the flow passage includes an upper surface that is located opposite to the flat surface region and that extends continuously and linearly from upstream of the obstacle to downstream of the powder containing cavity.

16. The medical dispenser of claim 4, wherein the flow passage includes an edge extending laterally across the flow passage and separating the flow passage-defining wall portion from the flat surface region.

* * * * *